United States Patent
Brand et al.

[11] Patent Number: 6,064,488
[45] Date of Patent: May 16, 2000

[54] METHOD AND APPARATUS FOR IN SITU GAS CONCENTRATION MEASUREMENT

[75] Inventors: Joel A. Brand, Colorado Springs; Garth A. Monlux, Castle Rock; Patrick Zmarzly, Boulder; Gregory J. Fetzer, Littleton; Benjamin C. Halsted, Littleton; Kenneth W. Groff, Littleton, all of Colo.; Jamine Lee, Burlington, Mass.; Neil Goldstein, Belmont, Mass.; Steven Richtsmeier, Tewksbury, Mass.; Fritz Bien, Concord, Mass.

[73] Assignee: Monitor Labs, Inc., Englewood, Colo.

[21] Appl. No.: 08/870,704

[22] Filed: Jun. 6, 1997

[51] Int. Cl.[7] .................................................. G01N 21/00
[52] U.S. Cl. .......................................... 356/440; 356/437
[58] Field of Search ..................................... 356/437–440

[56] References Cited

U.S. PATENT DOCUMENTS

| | | |
|---|---|---|
| 3,743,430 | 7/1973 | Riggs . |
| 4,297,035 | 10/1981 | Bjorklund .............................. 356/402 |
| 4,523,847 | 6/1985 | Bjorklund et al. ..................... 356/349 |
| 4,549,080 | 10/1985 | Baskins et al. ....................... 250/343 |
| 4,560,873 | 12/1985 | McGowan et al. ................. 250/339.09 |
| 4,594,511 | 6/1986 | Cooper et al. ..................... 250/339.07 |
| 4,684,258 | 8/1987 | Webster ................................ 356/409 |
| 4,726,644 | 2/1988 | Mathis ................................ 350/96.16 |
| 4,730,112 | 3/1988 | Wong ................................... 250/343 |
| 4,765,736 | 8/1988 | Gallagher et al. .................... 356/346 |
| 4,849,637 | 7/1989 | Cerff et al. ........................... 250/345 |
| 4,883,963 | 11/1989 | Kemeny et al. ................... 250/339.11 |
| 4,934,816 | 6/1990 | Silver et al. .......................... 356/409 |
| 4,937,448 | 6/1990 | Mantz et al. .......................... 250/343 |
| 4,941,747 | 7/1990 | Dakin ................................... 356/346 |
| 5,020,909 | 6/1991 | Landa .................................. 356/300 |
| 5,026,991 | 6/1991 | Goldstein et al. .................... 250/343 |
| 5,047,639 | 9/1991 | Wong ................................. 250/341.1 |
| 5,066,126 | 11/1991 | Hatori .................................. 356/328 |
| 5,093,743 | 3/1992 | Eng et al. ............................. 359/120 |
| 5,111,519 | 5/1992 | Mathis .................................. 385/24 |
| 5,125,051 | 6/1992 | Goutzoulis et al. .................... 385/27 |

(List continued on next page.)

OTHER PUBLICATIONS

Arndt, R., "Analytical Line Shapes for Lorentzian Signals Broadened by Modulation," *Journal of Applied Physics*, V. 35, No. 8, Aug. 1965, pp. 2522–2524.

Reid, J. et al., "High sensitivity pollution detection employing tunable diode lasers," *Applied Optics*, V. 17, No. 2, Jan. 15, 1978, pp. 300–307.

Reid, J. et al., "Second–Harmonic Detection with Tunable Diode Lasers—Comparison of Experiment and Theory," *Applied Physics*, Spring, 1981, B 26, pp. 203–210.

Bonse, D.S. et al., "Frequency modulation and wavelength modulation spectroscopies: comparison of experimental methods using a lead–salt diode laser," *Applied Optics*, V. 31, No. 6, Feb. 20, 1992, pp. 718–731.

Goldstein, N. et al., "Measurement of molecular concentrations and line parameters using line–locked second harmonic spectroscopy with AlGaAs diode laser," *Applied Optics*, V. 31, No. 18, Jun. 20, 1992, pp. 3409–3415.

Goldstein, N. et al., "Long–atmospheric–path measurements of near–visible absorption lines of $O_2$ isotopes and $H_2O$ with a prototype AlGaAs laser transceiver system," *Applied Optics*, V. 32, No. 30, Oct. 20, 1993, pp. 5849–5855.

*Primary Examiner*—Frank G. Font
*Assistant Examiner*—Amanda Merlino
*Attorney, Agent, or Firm*—Fields and Johnson, P.C.

[57] ABSTRACT

A method and apparatus for in situ measurement of the concentration of a gas with a frequency modulated tunable diode laser is disclosed. The sampling cell, which is mounted in the flow of gases to be measured, is a Herriott cell. Gas enters the sampling cell through sintered metal filters that prevent entrance of particulates. Signals from a sample detector and a null detector are compared to eliminate interference patterns from the laser optics. High accuracy dynamic calibration of the apparatus is also disclosed.

11 Claims, 3 Drawing Sheets

U.S. PATENT DOCUMENTS

| | | | |
|---|---|---|---|
| 5,125,747 | 6/1992 | Sayegh et al. | 356/407 |
| 5,136,671 | 8/1992 | Dragone | 385/46 |
| 5,173,749 | 12/1992 | Tell et al. | 356/437 |
| 5,173,794 | 12/1992 | Cheung et al. | 359/127 |
| 5,224,183 | 6/1993 | Dugan | 385/24 |
| 5,239,185 | 8/1993 | Ito et al. | 250/573 |
| 5,267,019 | 11/1993 | Whittaker et al. | 356/437 |
| 5,317,156 | 5/1994 | Cooper et al. | 205/345 |
| 5,317,379 | 5/1994 | Ryan et al. | 356/308 |
| 5,319,435 | 6/1994 | Melle et al. | 356/32 |
| 5,347,525 | 9/1994 | Faris | 372/19 |
| 5,436,459 | 7/1995 | Koch et al. | 250/373 |
| 5,444,528 | 8/1995 | Puschell | 356/73 |
| 5,469,265 | 11/1995 | Measures et al. | 356/419 |
| 5,473,719 | 12/1995 | Stone | 385/123 |
| 5,491,341 | 2/1996 | McCaul et al. | 250/343 |
| 5,499,313 | 3/1996 | Kleinerman | 385/12 |
| 5,526,155 | 6/1996 | Knox et al. | 359/130 |
| 5,528,040 | 6/1996 | Lehmann | 356/439 |
| 5,625,189 | 4/1997 | McCaul et al. | 356/437 |
| 5,818,578 | 10/1998 | Inman et al. | 356/440 |

METHOD AND APPARATUS FOR IN SITU GAS CONCENTRATION MEASUREMENT

TECHNICAL FIELD

The present invention relates to gas absorption spectroscopy, and more particularly to a method and apparatus for in situ tunable diode laser gas concentration measurement in a high temperature, harsh environment.

BACKGROUND ART

Gas spectroscopy measures the absorption of light by a gas sample. The absorption of a given wavelength of light can be measured to determine the concentration of a gas of interest in the sample.

In tunable diode laser absorption spectroscopy (TDLAS) a sample of the gas of interest in a reference cell as a wavelength reference is used to keep the laser line-locked to the linecenter of the absorption feature of interest. In frequency modulation spectroscopy (FMS) the laser is modulated across the absorption feature and the resulting signal is expanded in a Fourier Series. The coefficients of the expansion are denoted harmonics. The even harmonics each exhibit a maximum and the odd harmonics each exhibit a zero-crossing at the linecenter. Line-locking the laser to the feature of interest is accomplished by monitoring the third harmonic of the gas in the reference cell.

The sensitivity of TDLAS systems is often limited by interference patterns attributable to the optics of the system and by fluctuations in laser intensity, and more importantly by fluctuations in background levels of the second harmonic signal. Various prior art methods of eliminating interference patterns include mechanical approaches, specialized modulation waveforms, specialized modulation frequencies and multiple modulation frequencies. Fluctuations in second harmonic signals have been compensated by splitting the laser beam before the sampling cavity, and projecting one portion of the laser beam through the sampling cavity to a first detector and a second portion of the laser beam directly to a second detector. The second harmonic signal from each of these detector is then nomalized by dividing by the corresponding DC levels. In this manner, both fluctuations in laser intensity and second harmonic signal may be removed from the measurement. The paths of the first and second portions of the laser beams in such systems is typically significantly different.

In the past, TDLAS systems have typically extracted a sample for measurement into a remote measuring device. This approach requires pumps, filters and heated supply lines, adding complexity to and decreasing reliability of such a system. The accuracy of such remote measurement systems may be limited by absorption, desorption, precipitation or chemical reaction of the gas of interest in the delivery system.

An in situ measurement apparatus can be used to avoid the problems of extracting a sample and to measure the gas in an unperturbed environment. In an in situ measurement apparatus, the sampling cavity is mounted in the flow of gases in a stack or duct. Gas diffuses into the sampling cavity through filters that prevent particulates from entering the cavity. Particulates tend to settle on the reflective surfaces in the cavity and degrade the signal or damage the optical surfaces. In the past, ceramic filters were used; however, the porosity of ceramic filters is not easily controlled and the ceramic filters were difficult to integrate into the metal structure of the sampling cavity.

Previous in situ systems did not use TDLAS. These systems typically used a single reflector in the sampling cavity which limited the path length of the light beam in the sampling cavity and the accuracy of the apparatus.

DISCLOSURE OF THE INVENTION

A method and apparatus for in situ measurement of the concentration of a gas are disclosed. A tunable diode laser is tuned to the linecenter of a spectral feature of the gas of interest and modulated with a small AC current. The beam of the laser is projected to a beamsplitter that projects the beam through a reference cell to a reference detector, through an optical fiber and sampling cavity to a sample detector, and through the same optical fiber to a partially reflective surface which splits the beam and directs it to a null detector. The sampling cavity preferably is a Herriott cell incorporated into a probe that extends into the flow of the gas being measured. The probe is designed to control the rate of diffusion of gas into the sampling cavity, filter out particulates, withstand high temperature and vibration, and provide efficient in situ calibration. Calibration gas is heated to stack temperature for accurate calibration. The combination of sample signal and null signal, with the reference signal providing an accurate wavelength control, yields an accurate concentration measurement.

BRIEF DESCRIPTION OF THE DRAWINGS

Details of this invention are described in connection with the accompanying drawings that bear similar reference numerals in which.

DETAILED DESCRIPTION OF THE INVENTION

Figure 1:
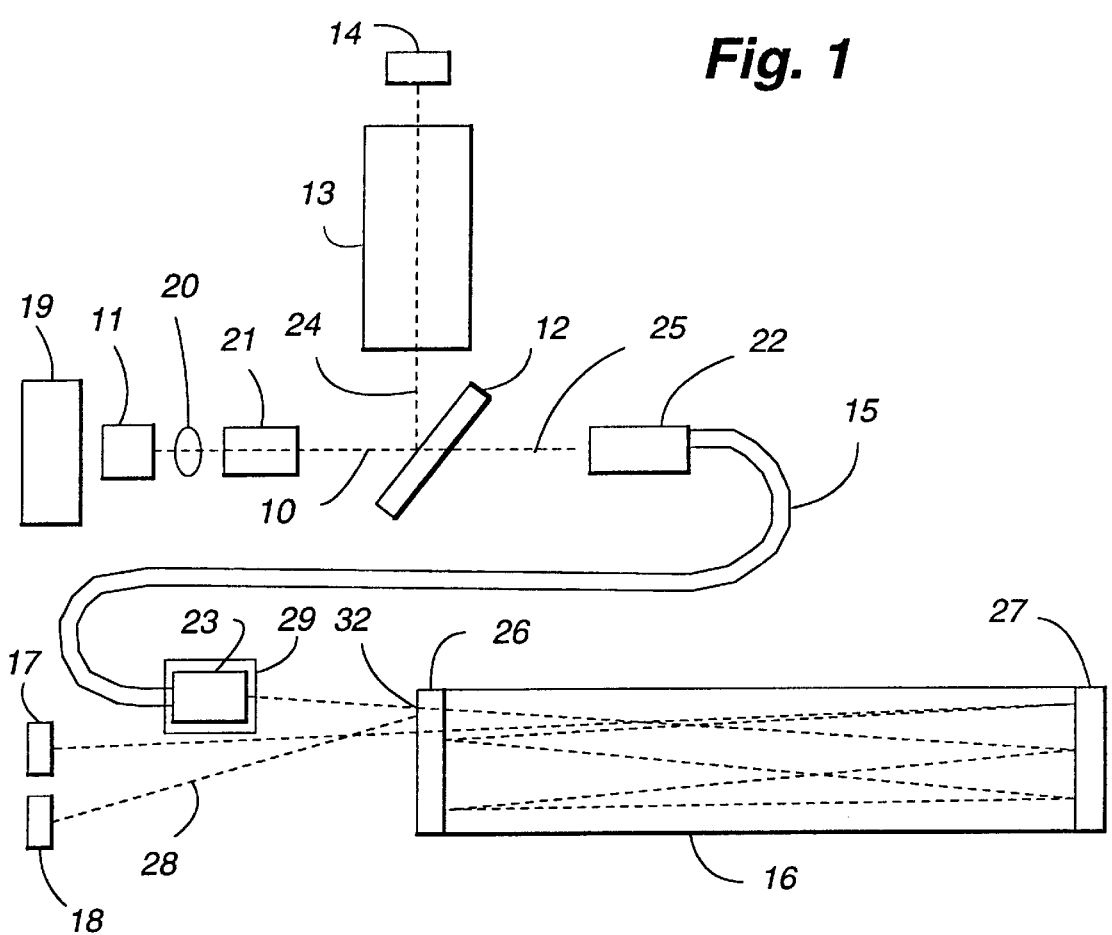
FIG. 1 is a schematic diagram showing an apparatus embodying features of the present invention.

Referring now to FIG. 1, the gas measurement apparatus shown, generally stated, includes a laser 11, a beamsplitter 12, a reference cell 13, a reference detector 14, an optical fiber 15, a sampling cavity 16, a sample detector 17 and a null detector 18. Laser 11 is preferably a distributed feedback (DFB) tunable diode laser wherein diffraction from an internal diffraction grating provides feedback that promotes accurate tuning. Other lasers, such as an external cavity feedback laser, a vertical cavity surface emitting laser (VCSEL), or even a multimode Fabry-Perot laser for strong absorption lines, would be suitable.

Laser 11, collimating optics 20, and optoisolator 21 all are thermally controlled. Temperature control of the diode laser 11 serves as a "coarse control" of the wavelength with a slow response time. Laser current serves as "fine control" with a very fast response time suitable for modulation. Thermal control of the focusing optics 20 and optoisolator 21 reduces drift in the instrument due to any thermally varying spurious signals resulting from interference patterns and optical feedback from the collimating lens upstream of the commercial optoisolator. Temperature control is achieved using one or more thermoelectric (TE) coolers 19.

Laser 11 projects a laser beam 10 into collimating optics 20. Collimating optics 20 collimates laser beam 10 into optoisolator 21. Optoisolator 21 acts as an optical diode, allowing light to pass in one direction and prevents light from passing in the opposite direction. Optoisolator 21 also prevents reflection of laser beam 10 back to laser 11 since such reflection would interfere with maintaining laser 11 at the wavelength of the spectral feature. Laser beam 10 is projected from optoisolator 21 to beamsplitter 12.

Beamsplitter 12 splits off a small amount of the laser beam 10, typically 4%, as reference beam 24, and uses reference beam 24 to precisely control the laser current to the desired operating wavelength. The preferred embodiment directs reference beam 24 through a reference cell 13 containing the species to be measured, typically at a pressure of 10 Torr, and monitors the third harmonic of the signal received from reference cell 13 by reference detector 14. This third harmonic signal is then used as an error signal in current control loop 64 to keep the laser 11 line-locked to the absorption line of interest.

Beamsplitter 12 transmits the remainder of laser beam 10 as sample beam 25 into first fiber collimator 22. First fiber collimator 22 focuses sample beam 25 into optical fiber 15 which projects the sample beam 25 to high temperature second fiber collimator 23. A second fiber collimator 23 collimates sample beam 25 and projects sample beam 25 into sampling cavity 16. Second fiber collimator 23 is mounted in a two axis flexure stage 29 designed for precision alignment of sample beam 25 into the sampling cavity 16.

Sampling cavity 16 shown is preferably a Herriott Cell with a spherical first reflector 26 and a spherical second reflector 27 with first reflector 26 and second reflector 27 being concave toward the interior of sampling cavity 16. Sample beam 25 enters sampling cavity 16 through a sampling cavity lens 32 which is directly in front of first reflector 26 and also serves to seal the sampling cavity 16. Sampling cavity 16 in the preferred embodiment is configured for 32 passes of 80 cm each pass.

Sample beam 25 exits sampling cavity 16 through sampling cavity lens 32 which helps focus the exiting sample beam 25 onto the sample detector 17. Sampling cavity lens 32 also provides enough curvature to deflect the first surface reflection of sample beam 25, as sample beam 25 enters sampling cavity 16, back as null beam 28 onto null detector 18 which is located near sample detector 17. Null beam 28 thus traverses the same path as the sample beam 25 except for the sampling cavity 16. Any signal arising from non-ideal laser characteristics, interference patterns in the source optics, fiber coupling, or other sources can be normalized and subtracted out of the sample beam 25 using the null detector 18. This improves the sensitivity of the instrument by a factor of approximately twenty.

Figure 2:
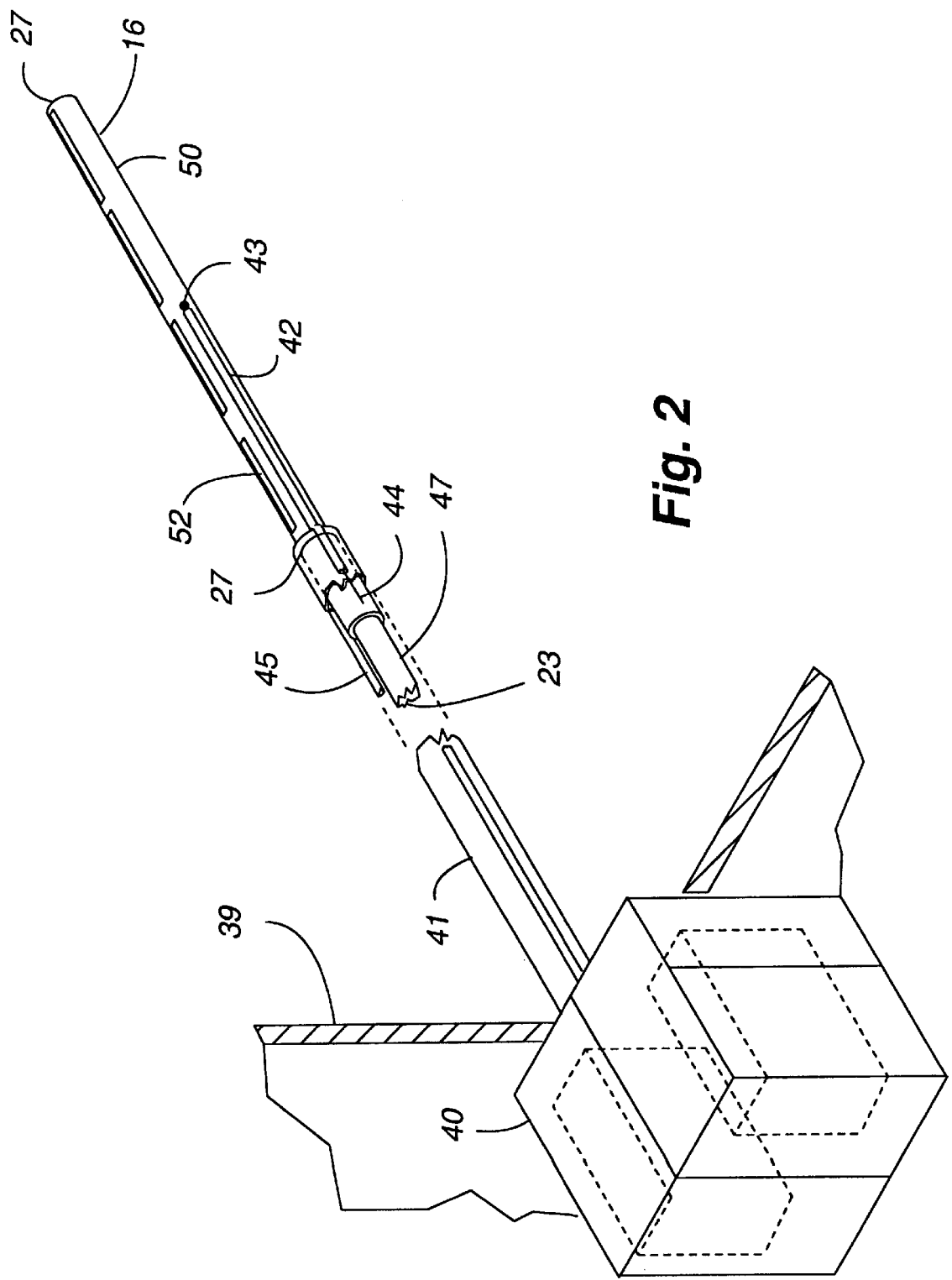
FIG. 2 is a broken away perspective view of an apparatus constructed in accordance with the present invention.

FIG. 2 shows apparatus embodying the present invention which includes enclosure 40 which mounts to the exterior of the wall 39 of the stack or duct through which the gases to be measured flow, weldment 41 in the form of an elongated metal tube that attaches to enclosure 40 and projects through wall 39 into the stack or duct, and sampling cavity 16 which extends from the end of weldment 41 opposite enclosure 40. Enclosure 40 is a hinged metal box, and laser 11, beamsplitter 12, reference cell 13, reference detector 14, thermoelectric cooler 19, focusing optics 20, optoisolator 21, first fiber collimator 22, sample detector 17 and null detector 18 are all mounted inside enclosure 40.

Sampling cavity 16 is mounted to and extends beyond the end of weldment 41 opposite enclosure 40, so that sampling cavity 16 is spaced away from wall 39 of the stack or duct. Sampling cavity 16 is, generally stated, a metallic cylinder 50. First reflector 26 is mounted at the end of cylinder 50 attached to weldment 41 and second reflector 27 is mounted at the opposite end of cylinder 50. Filters 52 are welded into slots relieved in the upper and lower surface of cylinder 50. Filters 52 allow gases from the stack or duct to diffuse into and out of sampling cavity 16 while preventing particulates from entering sampling cavity 16. Filters 52 are composed of sintered metal. The porosity, area and location of filters 52 determines the rate that gas diffuses through sampling cavity 16, thereby determining response time of the present invention.

The in situ design of sampling cavity 16 allows concentration measurement in an unperturbed environment. Containing the entire apparatus, including sampling cavity 16, within a metal enclosure which acts as a Faraday cage provides superior resistance to electrical interference.

Spacer assembly 47 is cylindrical and extends inside weldment 41 from cylinder 50 a portion of the distance to enclosure 40. Second fiber collimator 23 mounts on spacer assembly 47 at the end of spacer assembly furthest from cylinder 50. The mounting of second fiber collimator 23 provides accurate three axis adjustment so that sample beam 25 exiting second fiber collimator 23 can be precisely aligned with sampling cavity lens 32.

Calibration gas injection tube 42 extends from enclosure 40, along weldment 41, to the middle of cylinder 50. Calibration gas is pumped along calibration gas injection tube 42 from enclosure 40 into sampling cavity 16 to calibrate the apparatus in situ. The limited diffusion through filters 52 allows the sampling cavity 16 to be filled with calibration gas for accurate dynamic calibration of the apparatus. Calibration gas injection tube 42 runs along the outside of weldment 41 and calibration gas is heated to stack temperature by heat transfer from stack gases before injection into sampling cavity 16, providing accurate calibration of the apparatus.

Figure 3:
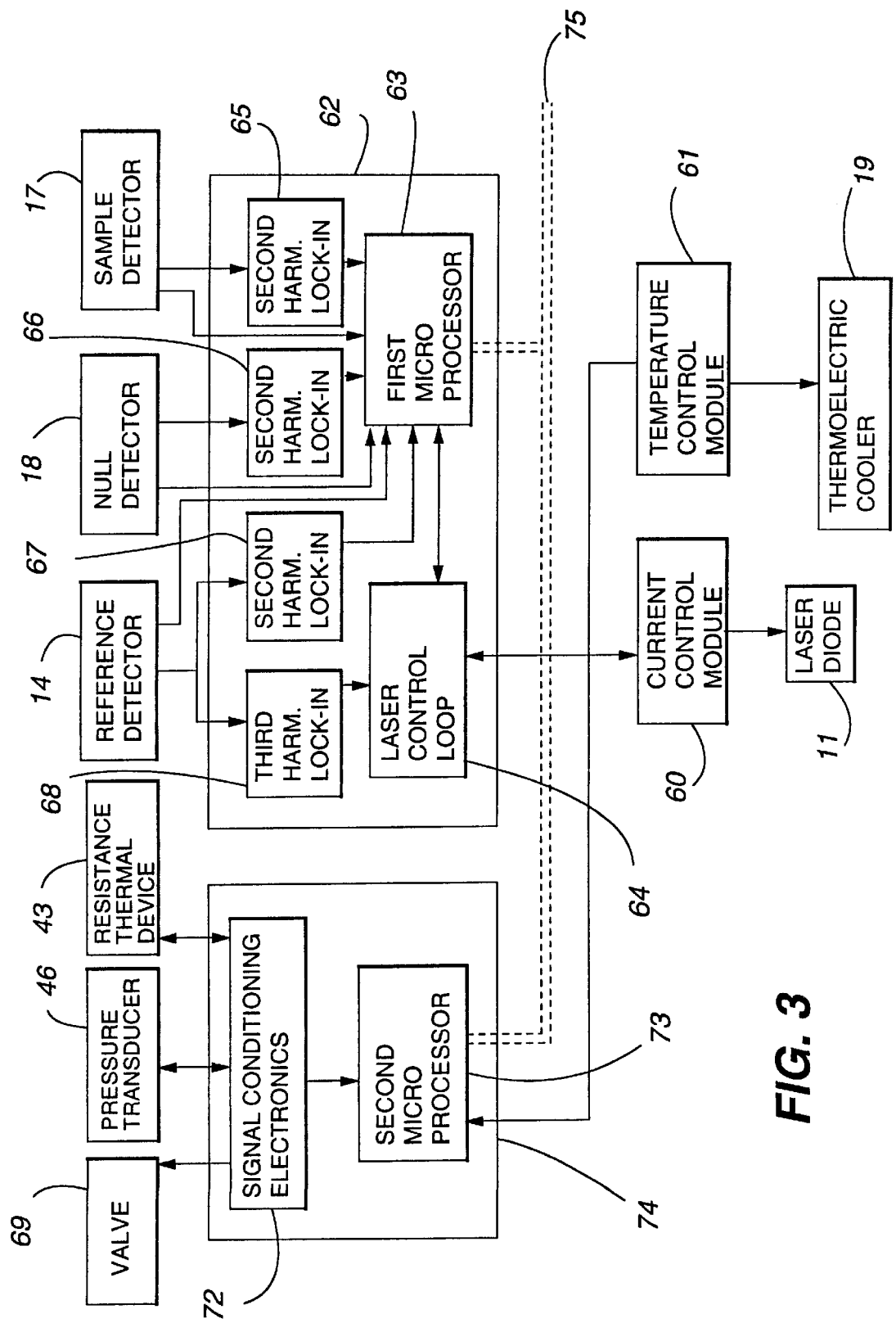
FIG. 3 is a block diagram of the electronic components of the apparatus embodying the present invention.

Referring now to FIG. 3, all of the below described electronic components are housed in enclosure 40 except resistance thermo device (RTD) 43.

Laser control is performed by a commercially available laser current control module 60 and laser temperature control module 61. The temperature control module 61 is set to a predetermined point for laser 11 to insure operation at the proper wavelength by controlling the current to the thermoelectric cooler 19 upon which laser 11 is mounted. The laser current is set to the precise value necessary to achieve line-locked operation by a voltage signal from analog signal processing board 62. Laser current control module 60 serves as a precise voltage controlled current source and also has many transient suppression and laser diode protection features. The modulated current is determined from looking at the second harmonic spectrum from the reference cell 13, performing a pattern recognition algorithm upon startup, and maintained there by the laser control loop 64. There are many gas absorption lines in the general area of interest, and the pattern recognition technique allows one to uniquely identify the one line of interest which has been characterized with respect to line width, interference, linestrength, temperature dependence, and pressure dependence. All of these functions, including the laser modulation, are performed on analog signal processing board 62, with the scanning controlled by a software resident on first microprocessor 63.

The raw detector signals from reference detector 14, sample detector 17 and null detector 18 are preamplified. The second harmonic of the signal from sample detector 17 is separated out by first lock-in amplifier 65 on analog signal processing board 62 and sent to first microprocessor 63, also on analog signal processing board 62. The second harmonic of the signal from null detector 18 is separated out by second lock-in amplifier 66 on analog signal processing board 62 and sent to first microprocessor 63. The second harmonic of the signal from reference detector 14 is separated out by third lock-in amplifier 67 on analog signal processing board 62 and sent to first microprocessor 63. First microprocessor 63 compares the null and sample second harmonics after normalization to their DC values, and sends raw concentration data via network connection 75 to second microprocessor 73 on sensor board 74. The second harmonic from the reference cell is used as a diagnostic value to ensure the laser is linelocked to the correct line and the system is operating properly.

The third harmonic component of the signal from reference detector 14 is separated out by fourth lock-in amplifier 68 on analog signal processing board 62 and sent to laser control loop 64 to lock laser 11 to the spectral feature of interest.

Second microprocessor 73 controls valves 69 through signal conditioning electronics 72, opening valve 69 to allow calibration gas to flow along calibration gas injection tube 42 to sampling cavity 16. Pressure in sampling cavity 16 is measured by pressure transducer 46 and temperature in sampling cavity 16 is measured by RTD 43. Signals from pressure transducer 46 and RTD 43 are conditioned by signal conditioning electronics 72 and sent to second microprocessor 73. Second microprocessor 73 uses the temperature and pressure measurement along with the raw concentration data from first microprocessor 63 to calculate the concentration of the gas of interest in sampling cavity 16. Network connection 75 which connects between first microprocessor 63 and second microprocessor 73 may also be connected to a display unit, a data storage device or a microprocessor that controls a combustion process.

Pressure tube 45, shown in FIG. 2, connects from pressure transducer 46 in enclosure 40 to sampling cavity 16. RTD 43 is mounted at the outlet of calibration gas injection tube 42 into sampling cavity 16, and is connected to signal conditioning electronics 72 by wires 44 which run through calibration gas injection tube 42.

The embedded software runs on first microprocessor 63 and second microprocessor 73. The first microprocessor 63 does the fast sampling of the lock-in signals and provides the raw concentration. The second microprocessor 73 handles the instrument calibration, and compensation.

The software controlling the laser 11 and performing the fast sampling is primarily concerned with calculating the raw concentration and ensuring the laser is operating properly. When the apparatus first starts, the apparatus waits until the laser temperature, as reported by the temperature control module 61, is within a set tolerance of the laser's 11 setpoint so that the coarse control of the laser wavelength is set to approximately the correct position. The exact tolerance depends on a number of factors of the thermal design, but is generally in the neighborhood of a tenth of a Kelvin. Once the temperature is correct, the software executes a routine to step the laser 11 through a set of operating current values, thus taking a high resolution spectral scan. The normalized second harmonic spectrum from the reference cell 13 is monitored and recorded. This spectrum is compared to one stored in memory and the proper operating current is then calculated so that the laser 11 is operating at the proper wavelength. Laser 11 is set to this wavelength and the intensity of the normalized second harmonic is then checked against a stored value to be sure that the laser 11 is operating at the right spectral feature. The intensity is checked once a minute during operation to be sure the laser 11 is always in the right place. The third harmonic control loop is turned on and the laser is line-locked and ready. Once the laser 11 is line-locked, first microprocessor 63 then calculates the normalized difference between the sample and null second harmonics and reports this value as the raw concentration.

The second microprocessor 73 takes this raw concentration and applies the proper pressure and temperature compensation curves to compensate the signal for variation in these parameters. The temperature compensation curves are dependent upon which absorption lines are chosen; for a given line they include temperature variation of linewidth and linestrength and are measured in the laboratory. They are typically represented by low order polynomials that fit over the region of interest. The compensation is performed by measuring the generic response of the concentration to temperature and pressure changes and then fitting this to curves. The values of these parameters at calibration is recorded and the correction factors are obtained by the ratio of the curve evaluated at the present values to that evaluated at the calibration values. In this manner, the curves need only compensate for changes from the values at calibration rather than in an absolute fashion, resulting in much less error. Calibration is performed in the standard fashion by injection of two concentrations, typically zero and a value near the highest anticipated measurement, with gains and offsets thus calculated to convert raw concentrations into calibrated concentrations. The second harmonic measurement technique is inherently linear in the regime of weak absorptions and no correction for non-linearity is normally used for operation within the specified operating ranges. The software is configured so that the user may enter various calibration times and values, and control whether or not to readjust the calibration parameters or merely check that the instrument reads correctly. The second microprocessor 73 samples the values from the pressure transducer 46 and RTD 43 for signal compensation and also for diagnostics.

Although the present invention has been described with a certain degree of particularity, it is understood that the present disclosure has been made by way of example and that changes in details of structure may be made without departing from the spirit thereof.

What is claimed is:

1. Apparatus for measuring concentration of a gas comprising:

a tunable diode laser, said laser being tuned to project a laser beam at the wavelength of a spectral feature of said gas, said laser beam being modulated;

a sampling cavity having a first end and a second end, said first and second ends having opposed interior reflecting surfaces;

a lens attached to said first end, said laser beam being projected onto said lens, said lens splitting said laser beam, deflecting a first surface reflection of said laser beam and projecting said laser beam into said sampling cavity;

a null detector receiving said first surface reflection, said null detector measuring intensity of said first surface reflection and producing an electrical null signal proportional to said intensity;

a sample detector, said laser beam being reflected a plurality of times in said sampling cavity by said first and second ends and projected back through said lens to said sample detector wherein said lens helps focus said laser beam on said sample detector, said sample detector measuring intensity of said laser beam and producing an electrical sample signal proportional to said intensity, said sample detector being located near said null detector so that the path of said laser beam to said sample detector and the path of said laser beam to said null detector differ only by the path of the laser beam inside the sampling cavity; and a microprocessor receiving and comparing said sample signal and said null signal to eliminate influence of laser beam variations and interference patterns.

2. Apparatus, as set forth in claim 1, further comprising:

a beamsplitter upon which said laser beam is projected, said beamsplitter splitting said laser beam into a reference beam and a sample beam, said sample beam being projected onto said lens;

a reference cell containing a predetermined concentration of said gas, said reference beam being projected from said beamsplitter through said reference cell; and a reference detector receiving said reference beam from said reference cell, said reference detector measuring intensity of said reference beam and producing an electrical reference signal proportional to said intensity, a third harmonic of said reference signal line locking said laser to said wavelength and said microprocessor comparing a second harmonic of said sample signal and a second harmonic of said null signal to calculate concentration of said gas in said sampling cavity.

3. Apparatus, as set forth in claim 2, further comprising:

an enclosure, said enclosure being attached to the outside of a wall of an exhaust stack and housing said laser, said reference cell, said reference detector, said sample detector, said null detector and said microprocessor; and a weldment attached to said enclosure and projecting through said wall of said exhaust stack into the interior of said exhaust stack, said sampling cavity being mounted on said weldment on an end of said weldment furthest from said wall of said exhaust stack so that said sampling cavity is spaced away from said wall of said exhaust stack.

4. Apparatus, as set forth in claim 1, wherein said sampling cavity includes:

a cylindrical metal body, said first sampling cavity end mounting to a first end of said body and said second sampling cavity end mounting to a second end of said body, said body having filters, said filters allowing exhaust gases from said exhaust stack to diffuse into said sampling cavity and preventing particulates from entering into said sampling cavity.

5. Apparatus, as set forth in claim 4, further comprising:

a calibration gas injection tube attached to and opening into an intermediate portion of said body of said sampling cavity at a first tube end and attached to said enclosure at a second tube end, with calibration gas flowing in said tube from said enclosure to said sampling cavity being heated by heat transfer from said exhaust gases to the temperature of said exhaust gases.

6. Apparatus for measuring concentration of a gas comprising:

a tunable diode laser, said laser being tuned to project a laser beam at the wavelength of a spectral feature of said gas, said laser beam being modulated;

a beamsplitter upon which said laser beam is projected, said beamsplitter splitting said laser beam into a reference beam and a sample beam;

a sampling cavity having a first end and a second end, said first and second ends having opposed interior reflecting surfaces, said sampling cavity including a cylindrical metal body, said first sampling cavity end mounting to a first end of said body and said second sampling cavity end mounting to a second end of said body, said body having filters, said filters allowing exhaust gases from an exhaust stack to diffuse into said sampling cavity and preventing particulates from entering into said sampling cavity;

a lens attached to said first end, said sample beam being projected from said beamsplitter into said sampling cavity through said lens, said lens deflecting a first surface reflection;

a null detector receiving said first surface reflection, said null detector measuring intensity of said first surface reflection and producing an electrical null signal proportional to said intensity;

a sample detector, said sample beam being reflected a plurality of times in said sampling cavity by said first and second ends and projected back through said lens to said sample detector wherein said lens helps focus said laser beam on said sample detector, said sample detector measuring intensity of said sample beam and producing an electrical sample signal proportional to said intensity, said sample detector being located near said null detector so that the path of said sample beam to said sample detector and the path of said sample beam to said null detector differ only by the path of the sample beam inside the sampling cavity; and a reference cell containing a predetermined concentration of said gas, said reference beam being projected from said beamsplitter through said reference cell; and a reference detector receiving said reference beam from said reference cell, said reference detector measuring intensity of said reference beam and producing an electrical reference signal proportional to said intensity, a third harmonic of said reference signal line locking said laser to said wavelength;

a microprocessor receiving and comparing said sample signal and said null signal to eliminate laser beam variations and interference patterns between said laser and said lens and said fiber, said microprocessor comparing a second harmonic of said reference signal with said second harmonic of said sample signal and said second harmonic of said null signal to calculate concentration of said gas in said sampling cavity;

an enclosure, said enclosure being attached to the outside of a wall of said exhaust stack and housing said laser, said reference cell, said reference detector, said sample detector, said null detector and said microprocessor;

a weldment attached to said enclosure and projecting through said wall of said exhaust stack into the interior of said exhaust stack, said sampling cavity being mounted on said weldment on an end of said weldment furthest from said wall of said exhaust stack so that said sampling cavity is spaced away from said wall of said exhaust stack; and a calibration gas injection tube attached to and opening into an intermediate portion of said body of said sampling cavity at a first tube end and attached to said enclosure at a second tube end, with calibration gas flowing in said tube from said enclosure to said sampling cavity being heated by heat transfer from said exhaust gases to the temperature of said exhaust gases.

7. A method of measuring concentration of a gas in an exhaust stack comprising the steps of:

tuning a laser to project a laser beam at the wavelength of a spectral feature of the gas;

projecting the laser beam onto a lens which is attached to a sampling cavity containing exhaust gases from the exhaust stack;

detecting a first portion of the laser beam at a first position, the first portion being a first surface refection of the laser beam off the lens;

passing a second portion of the laser beam through the lens into the sampling cavity;

reflecting the second portion of the laser beam a plurality of times between a first end of the sampling cavity and a second end of the sampling cavity;

passing the second portion of the laser beam out of the sampling cavity and back through the lens;

focusing the second portion of the laser beam as it passes back through the lens:

detecting the second portion of the laser beam at a second position located near the first position detector so that the difference in the path of the first portion of the laser beam and the path of the second portion of the laser beam is the path of the second portion of the laser beam in the sampling cavity; and comparing the first and second portions of the laser beam to calculate said concentration of the gas in the exhaust stack.

8. The method, as set forth in claim 7, further comprising the step of:

diffusing the exhaust gases into the sampling cavity at the temperature and pressure of the exhaust gases while preventing particulates from entering the sampling cavity.

9. The method, as set forth in claim 8, further comprising the steps of:

projecting a third portion of the laser beam through a reference cell; and detecting the third portion of the laser beam to lock the laser to the wavelength.

10. The method, as set forth in claim 9, wherein:

the step of detecting a first portion of the laser beam includes detecting the intensity of the first portion of the laser beam with a first photodetector, converting the first portion of the laser beam into an electrical first signal proportional to the intensity and separating a second harmonic of the first signal with a first lock-in amplifier;

the step of detecting a second portion of the laser beam includes detecting the intensity of the second portion of the laser beam with a second photodetector, converting the second portion of the laser beam into an electrical second signal proportional to the intensity and separating a second harmonic of the second signal with a second lock-in amplifier recording the DC valve of the signal to the second harmonic signal; and the step of comparing includes comparing the second harmonic of the first signal and the second harmonic of the second signal.

11. A method of measuring concentration of a gas in an exhaust stack comprising the steps of:

diffusing exhaust gases from the exhaust stack into a sampling cavity at the temperature and pressure of the exhaust gases while preventing particulates from entering the sampling cavity;

tuning a laser to project a laser beam at the wavelength of a spectral feature of the gas;

projecting the laser beam onto a lens which is attached to the sampling cavity;

detecting intensity of a first portion of the laser beam at a first photodetector, said first portion being a first surface refection of the laser beam off the lens;

converting said first portion of said laser beam into an electrical first signal proportional to said intensity;

recording the DC value of the signal to properly scale the second harmonic signal;

separating a second harmonic of the first signal with a first lock-in amplifier;

passing a second portion of the laser beam through the lens into said sampling cavity;

reflecting the second portion of said laser beam a plurality of times between a first end of the sampling cavity and a second end of the sampling cavity;

passing the second portion of the laser beam out of the sampling cavity and back through the lens;

focusing the second portion of the laser beam as it passes back through the lens;

detecting intensity of the second portion of the laser beam at a second photodetector located near the first photodetector so that the difference in the path of the first portion of the laser beam and the path of the second portion of the laser beam is the path of the second portion of the laser beam in the sampling cavity;

converting the second portion of the laser beam into an electrical second signal proportional to the intensity of the second portion of the laser beam;

separating a second harmonic of the second signal with a second lock-in amplifier;

projecting a third portion of the laser beam through a reference cell; and detecting the third portion of the laser beam to lock the laser to said wavelength.

* * * * *